(12) United States Patent
Krok et al.

(10) Patent No.: US 10,532,455 B1
(45) Date of Patent: Jan. 14, 2020

(54) ERGONOMIC HANDLE ADAPTED FOR USE WITH A HAND-OPERATED PERSONAL USE DEVICE

(71) Applicants: Paul Krok, Culver City, CA (US); Brian Steinhobel, Sandton (ZA)

(72) Inventors: Paul Krok, Culver City, CA (US); Brian Steinhobel, Sandton (ZA)

(73) Assignee: Bonfit America Inc., Culver City, CA (US)

( * ) Notice: Subject to any disclaimer, the term of this patent is extended or adjusted under 35 U.S.C. 154(b) by 202 days.

(21) Appl. No.: 15/853,450

(22) Filed: Dec. 22, 2017

Related U.S. Application Data (60) Provisional application No. 62/438,984, filed on Dec. 23, 2016.

(51) Int. Cl.
| | | |
|---|---|---|
| *B25G 1/10* | (2006.01) | |
| *A61C 17/02* | (2006.01) | |
| *A61B 17/24* | (2006.01) | |
| *B26B 21/52* | (2006.01) | |

(52) U.S. Cl.
CPC ............ *B25G 1/102* (2013.01); *A61B 17/244* (2013.01); *A61C 17/0202* (2013.01); *B25G 1/10* (2013.01); *B26B 21/522* (2013.01)

(58) Field of Classification Search
CPC ... B25G 1/00; B25G 1/01; B25G 1/02; B25G 1/10; B25G 1/102; A61B 17/244; A61C 17/0202; B26B 21/522
USPC .......................................... 16/422, 426, 430
See application file for complete search history.

(56) References Cited

U.S. PATENT DOCUMENTS

| | | | | | |
|---|---|---|---|---|---|
| 2,263,885 | A * | 11/1941 | McGauley | ............... | A46B 5/02 15/143.1 |
| 2,382,304 | A * | 8/1945 | Foltz | ......................... | B26B 3/00 30/343 |
| 4,548,248 | A * | 10/1985 | Riemann | ................ | B25G 1/102 30/308 |
| 4,785,495 | A * | 11/1988 | Dellis | .................... | B25G 1/102 16/421 |
| 5,440,784 | A * | 8/1995 | Hull | ....................... | A01K 87/08 16/114.1 |
| 5,816,337 | A * | 10/1998 | Kun-Chuan | ........... | A01B 1/222 172/372 |
| 8,402,864 | B1 * | 3/2013 | Stephens | ................. | B25B 23/18 81/177.2 |
| 8,616,098 | B1 * | 12/2013 | Rosow | .................... | B25G 1/102 16/430 |
| 2008/0141536 | A1 * | 6/2008 | Gratsias | ................ | B26B 21/522 30/32 |
| 2011/0061204 | A1 * | 3/2011 | Schulz | .................. | B26B 21/522 16/430 |

* cited by examiner

*Primary Examiner* — Roberta S Delisle
(74) *Attorney, Agent, or Firm* — Thomas I. Rozsa (57) ABSTRACT

An ergonomic handle to be used in conjunction with a hand-operated personal use tool. A unique feature of the ergonomic handle is a series of concave-shaped grooves and convex-shaped protrusions on the top surface and one concave-shaped groove and two convex-shaped protrusions on the bottom surface. The ergonomic handle has an arcuate shape to facilitate a secure grasping of the handle by the fingers of one handle.

19 Claims, 9 Drawing Sheets

ERGONOMIC HANDLE ADAPTED FOR USE WITH A HAND-OPERATED PERSONAL USE DEVICE

CROSS-REFERENCE TO RELATED APPLICATION

This patent application claims priority to Provisional Application No. 62/438,984 filed on Dec. 23, 2017.

BACKGROUND OF THE INVENTION

1. Field of the Invention

The present invention relates to the field of hand-operated devices which are used for personal care such as tongue scrapers, toothbrushes, safety razors, dental picks which dispense water, dental air flossers etc.

2. Description of the Prior Art

To the best of the inventors' knowledge, there is no prior art that is relevant to the present invention.

SUMMARY OF THE INVENTION

The present invention is a handle to be used in conjunction with a hand-operated personal use tool selected from the group consisting of tongue scrapers, toothbrushes, safety razors, dental picks which dispense water, dental air flossers etc. For purposes of the present invention, the operative portion to which the present invention handle is attached is illustrated as a tongue scraper which is illustrated in dashed lines and it is the unique features of the handle that are being claimed as the innovation. The tongue scraper illustrated in dashed lines can be replaced with other operative devices identified in this paragraph. In addition to a personal use tool, the present invention ergonomic handle can be used with any other handheld object and therefore defined more broadly, the present invention is an ergonomic handle to be used with an object.

Most handles for tools such as a toothbrush, safety razor or tongue scraper are typically straight and do not accommodate the fingers of a hand to be placed within the handle portion so that the handle can be more securely gripped. The present invention also has the unique feature of having a series of concave-shaped grooves and convex-shaped protrusions on the top surface and one concave-shaped groove and two convex-shaped protrusions on the bottom surface. The ergonomic handle has an arcuate shape to facilitate a secure grasping of the handle by the fingers of one hand. Together, these grooves and protrusions provide a more ergonomically useable handle for both a right-handed person and a left-handed person.

Specifically, the handle consists of five cavities and six protrusions on the top surface. The proximal end of the first protrusion is adjacent the base of the tool, and each cavity has a protrusion on opposite longitudinal sides of a cavity. Described sequentially beginning with the protrusion adjacent the dashed lines, there is a first top protrusion, a first top cavity, a second top protrusion, a second top cavity, a third top protrusion, a third top cavity, a fourth top protrusion number, a fourth top cavity, a fifth top protrusion; a fifth top cavity, and a sixth top protrusion.

The bottom surface is generally arcuate. The first top protrusion is enveloped on the body of the ergonomic handle and does not extend to the bottom surface. The first top cavity extends through the body of the ergonomic handle and is aligned with a first bottom protrusion. The second top protrusion is aligned with and forms a beginning of a first and only bottom cavity which is also aligned with the second top cavity. The third top protrusion is aligned with the distal end of the first and only bottom cavity which in turn extends to a second bottom protrusion. The remainder of the bottom surface is flat to the tip which ends in a sixth top protrusion on the upper surface.

The ergonomic handle is held by the fingers of one hand, either left hand or right hand. A right-handed person or left-handed person will place a forefinger in the first top cavity, a third or middle finger in the second top cavity, a fourth or ring finger in the fourth cavity and the fifth or pinky finger in the fifth top cavity. The thumb is placed anywhere on the lower surface, preferably in the first and only bottom cavity. Alternatively, still held in this configuration, a forefinger is placed in the second top cavity, a third or middle finger is placed in the second top cavity, a fourth or ring finger is placed in the fourth top cavity and the fifth or pinky finger placed in the fifth top cavity. The thumb is placed anywhere on the lower surface, preferably into the bottom cavity.

The handle therefore enables a person to grip a personal use device with the hand in a much more secure manner than prior art handles. For example, a tongue scraper is typically made of plastic and gripped with the thumb and forefinger only. Other devices are tubular and need to be gripped by the hand by securely gripping the portion without having appropriate cavities to facilitate correct placement of the different fingers of a person's hand.

It is therefore an object of the present invention to provide a novel handle for a hand-operated personal use device or tool which facilitates a secure grip on the handle so that the personal use tool can be safely operated.

The ergonomic handle is arcuate when viewed from the side.

While the personal use device or tool is primarily used for non-electrical products such as a tongue scraper, it can also be incorporated into a motorized product such as air flosser. In addition, while the majority of this disclosure focuses on personal use tools as defined above, it will be appreciated that it is within the spirit and scope of the present invention for the novel, non-obvious ergonomic handle to be useable with any hand-held object in addition to the previously defined personal use tool.

Defined in detail, the present invention is an ergonomic handle adapted for use with a hand-operated personal use tool comprising: (a) a top surface and a bottom surface having a generally arcuate shape; (b) said ergonomic handle having a first end and a second end with a body in between said first end and said second end; (c) said first end affixed to said hand-operated personal use tool; (d) between the first end and the second end, the top surface of the ergonomic handle includes five spaced apart cavities and six spaced apart protrusions, which sequentially are a first top protrusion beginning at said front end, a first top cavity, a second top protrusion, a second top cavity, a third top protrusion, a third top cavity, a fourth top protrusion, a fourth top cavity, a fifth top protrusion, a fifth top cavity and a sixth top protrusion terminating in said rear end; (e) the bottom surface is generally arcuate, the first top protrusion is enveloped on and within the body of the ergonomic handle and does not extend to the bottom surface, the first top cavity extends through the body of the ergonomic handle to the bottom surface to form a first bottom protrusion, the second top protrusion beginning at the bottom of the first cavity is aligned with the second top cavity and extends to the second bottom protrusion, a third top protrusion is aligned with the second bottom protrusion, a remainder of the bottom surface is flat and extends the second end which on the upper surface ends in the sixth top protrusion; and (f) said ergonomic handle is outlined with a smooth sidewall extending along an entire circumference of the ergonomic handle.

Defined more broadly, the present invention is an ergonomic handle comprising: (a) an upper surface and a lower surface; (b) said ergonomic handle having a first end and a second end with a body in between said first end and said second end; (c) said first end affixed to an object; (d) said upper surface of said ergonomic handle including five spaced apart cavities formed into the upper surface of said body and aligned along said upper surface; and (e) said upper surface of said ergonomic handle including six spaced apart protrusions with a first protrusion adjacent said front end, a sixth protrusion adjacent said rear end, and a second through fourth protrusion respective spaced between a second and third cavity, a third and fourth cavity, and a fourth and fifth cavity.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

The broken lines shown are for environmental purposes only and form no part of the claimed invention.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
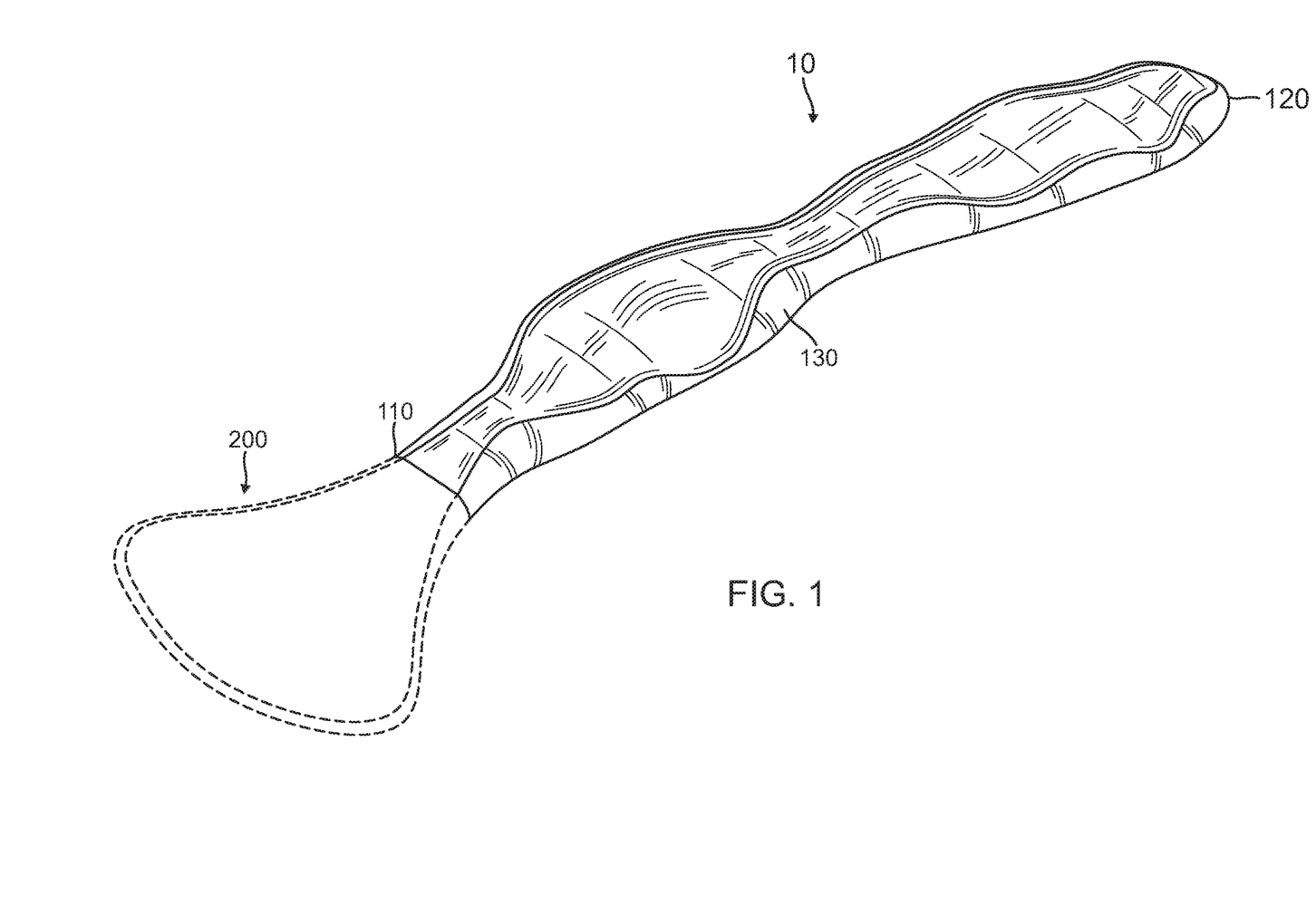
FIG. 1 is a top and left side perspective view of the present invention ergonomic handle adapted for use with a hand-operated personal use tool.
Figure 2:
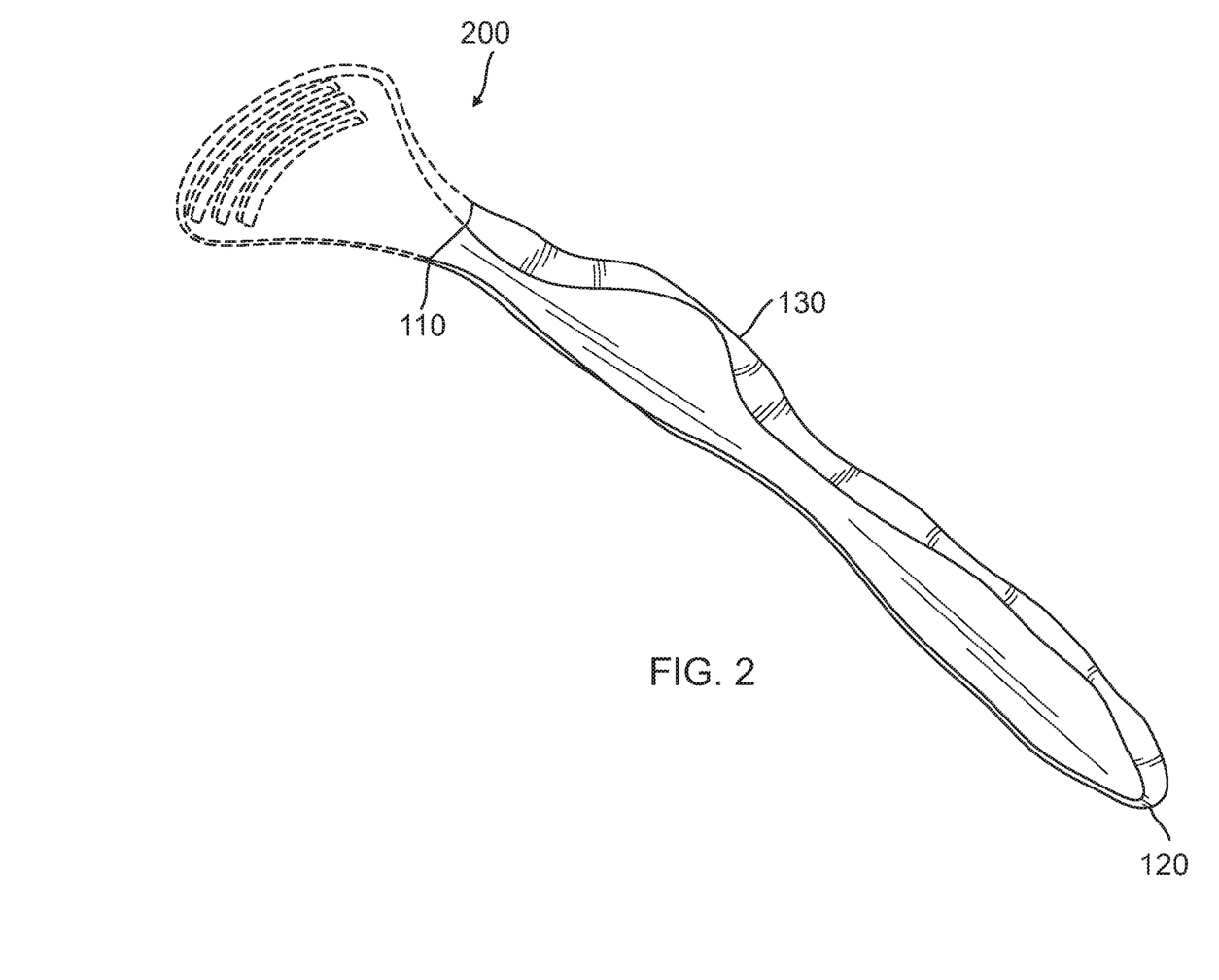
FIG. 2 is a bottom and right side perspective view of the ergonomic handle adapted for use with a hand-operated personal use tool.

Referring to FIGS. 1 and 2, there is illustrated the present invention ergonomic handle 10 having a first end (also alternatively called front or front end) 110 and a second end (alternatively called rear end or tip) 120 with a body 130 in between the first end 110 and the second end 120. The first end 110 is affixed to said specific hand-operated personal use tool, which in the example is a tongue scraper 200. The tool 200 used with the hand-operated personal use ergonomic handle 10 is selected from the group consisting of tongue scrapers, tooth brushes, safety razors, dental picks which dispense water and dental air flossers. It also within the spirit and scope of this invention to include other hand-operated personal use tools to be used with the present invention ergonomic handle 10. The tool 200 is illustrated in dashed lines and therefore specifically forms no portion of the present invention as it is the ergonomic handle 10 that is being claimed as the innovative feature of the present invention.

Figure 3:
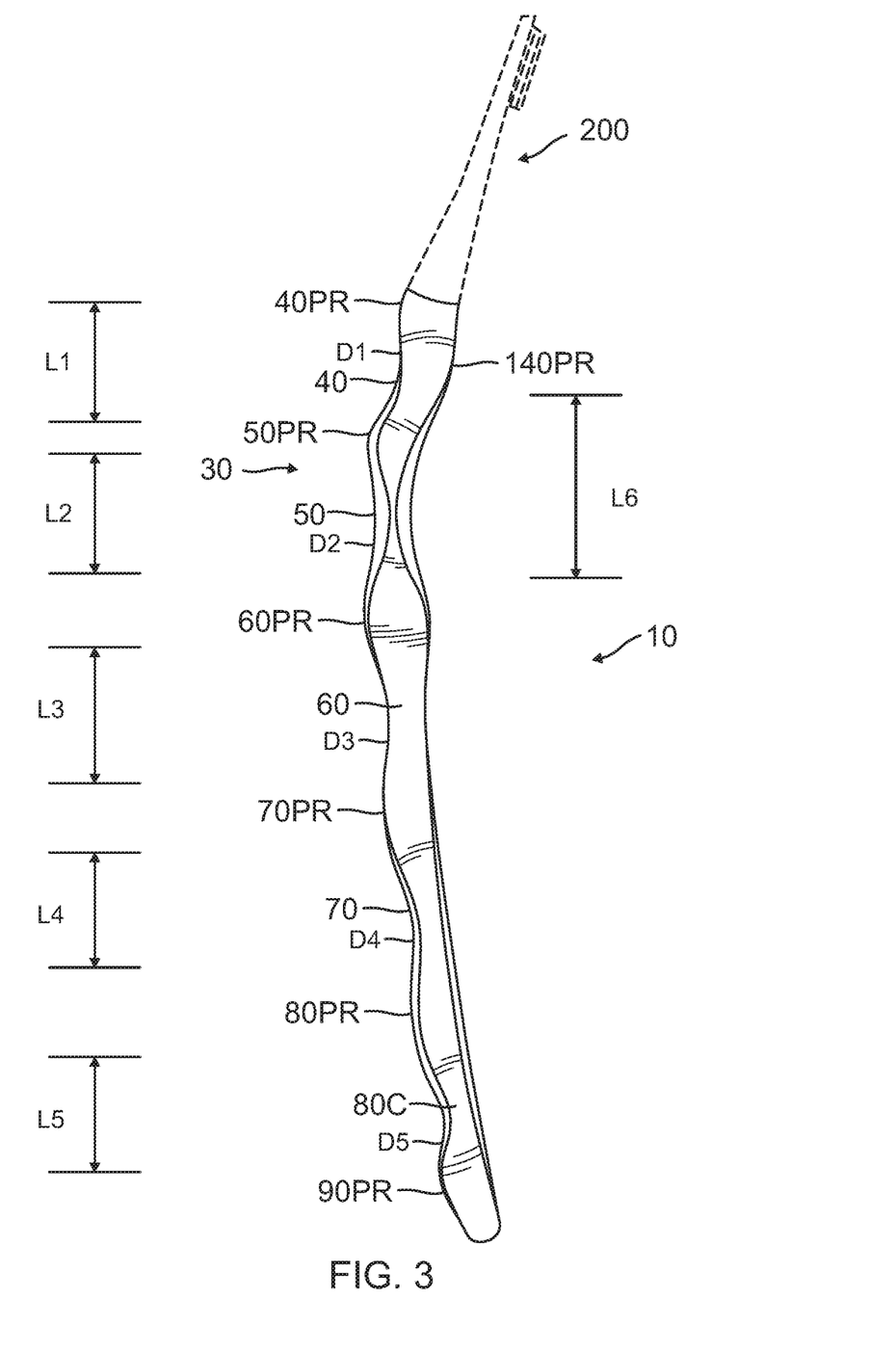
FIG. 3 is a left side elevational view of the ergonomic handle for a hand-operated personal use tool.
Figure 4:
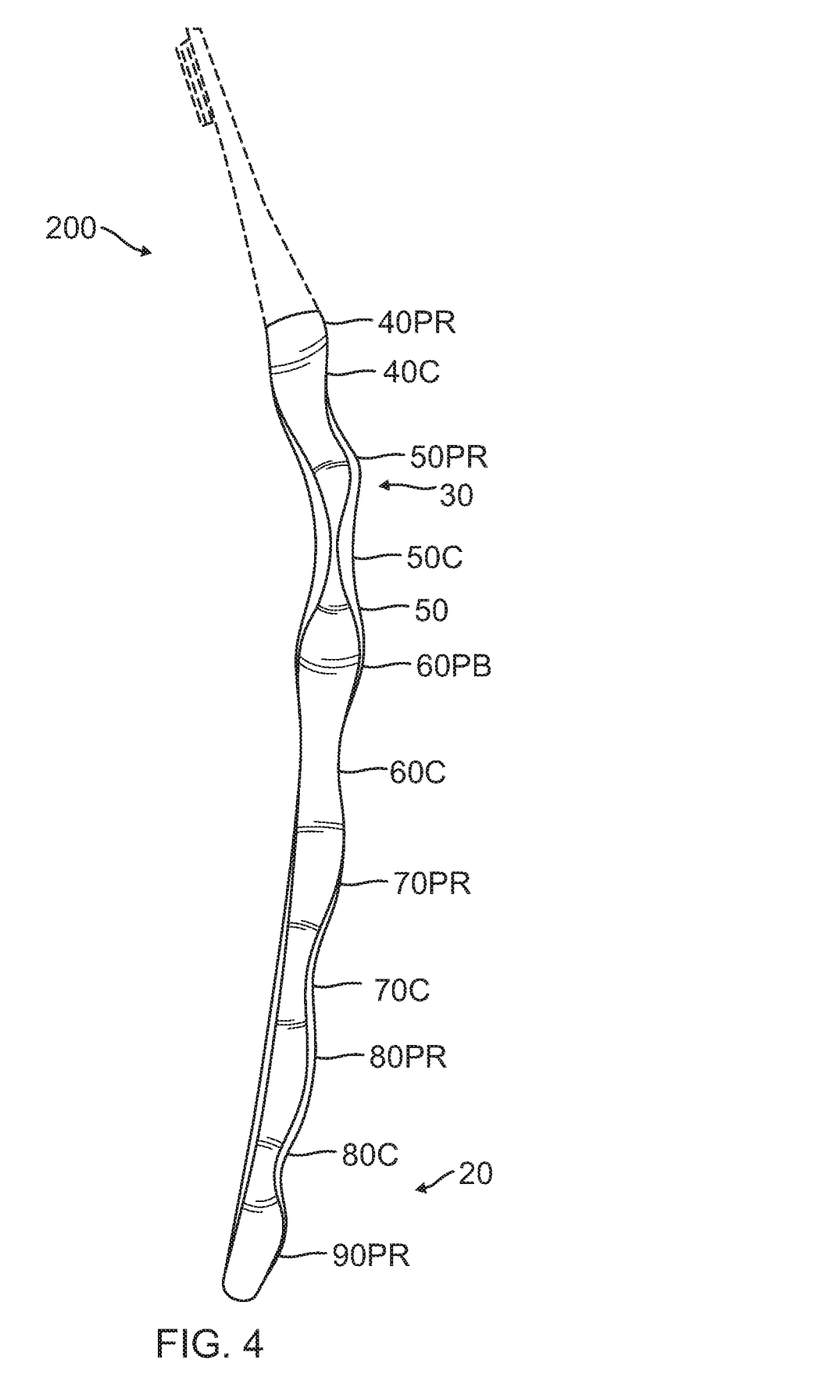
FIG. 4 is a right side elevational view of the ergonomic handle for a hand-operated personal use tool.

Referring to FIGS. 3 and 4, the present invention ergonomic handle 10 is illustrated in a left side view (FIG. 3) and a right side view (FIG. 4). As best illustrated in the side views of FIGS. 3 and 4, the present invention ergonomic handle 10 for a hand-operated personal use tool 200 (illustrated in dashed lines—representing a tongue scrapper) has an arcuate shape with a first end 110 and a second end 120. The ergonomic handle 10 has a top surface 20 and a bottom surface 30. Between first end 110 and second end 120, the top surface 20 of the ergonomic handle 10 comprises five cavities and six protrusions on the top surface 20. The first protrusion begins adjacent the front end 100, and each cavity has a protrusion on opposite longitudinal sides of a respective cavity. Described sequentially beginning with the protrusion adjacent the front end 110, there is first top protrusion 40PR, a first top cavity, a second top protrusion, a second top cavity, a third top protrusion, a third top cavity, a fourth top protrusion, a fourth top cavity, a fifth top protrusion, a fifth top cavity, and a sixth top protrusion 90PR terminating in rear end 120. The bottom surface 30 is generally arcuate. The first top protrusion 40PR is enveloped into the body 130 of the ergonomic handle 10 and does not extend to the bottom surface 30. The first top cavity number 40C extends into the body 130 of the ergonomic handle 10 and is partially aligned with the first bottom protrusion. The second top protrusion is aligned with a portion of the first bottom cavity which is also aligned the with second top cavity and extends to the second bottom protrusion. The third top protrusion is aligned with the second bottom protrusion. The remainder of the bottom surface 30 is flat to the tip 120 which on the upper surface 20 ends in sixth top protrusion number 90PR.

The bottom surface 30 is arcuate beginning with an angle "A" of approximately fifteen (15) degrees relative to an imaginary horizontal line relative to bottom surface 30 and ending at an angle "B" of approximately fifteen (15) degrees relative to an imaginary horizontal line relative to bottom surface 30.

Referring to FIG. 3, first top cavity 40C has an approximate length L1 of 0.5 inches and an approximate depth D1 of 0.1 inches. The other cavities located on upper surface 30 have approximate lengths and approximate depths as follows: second top cavity 50C has a length L2 of 0.65 inches and a D2 depth of 0.15 inches, third top cavity 60C has a length L3 of 0.65 inches and a depth D3 of 0.15 inches, fourth top cavity 70C has a length L4 of 0.55 inches and a depth D4 of 0.12 inches and fifth top cavity 80C has a length L5 of 0.4 inches and a depth D5 of 0.1 inches. First bottom cavity 150C of bottom surface 30 has a length L6 between 0.8 inches and 1.5 inches with a preferred length of approximately 0.9 inches and a depth between 0.1 inches and 0.2 inches and a preferred depth of approximately 0.15 inches. These dimensions given are a preferred example and it is within the spirit and scope of this invention for theses dimensions to be smaller or larger.

Figure 9:
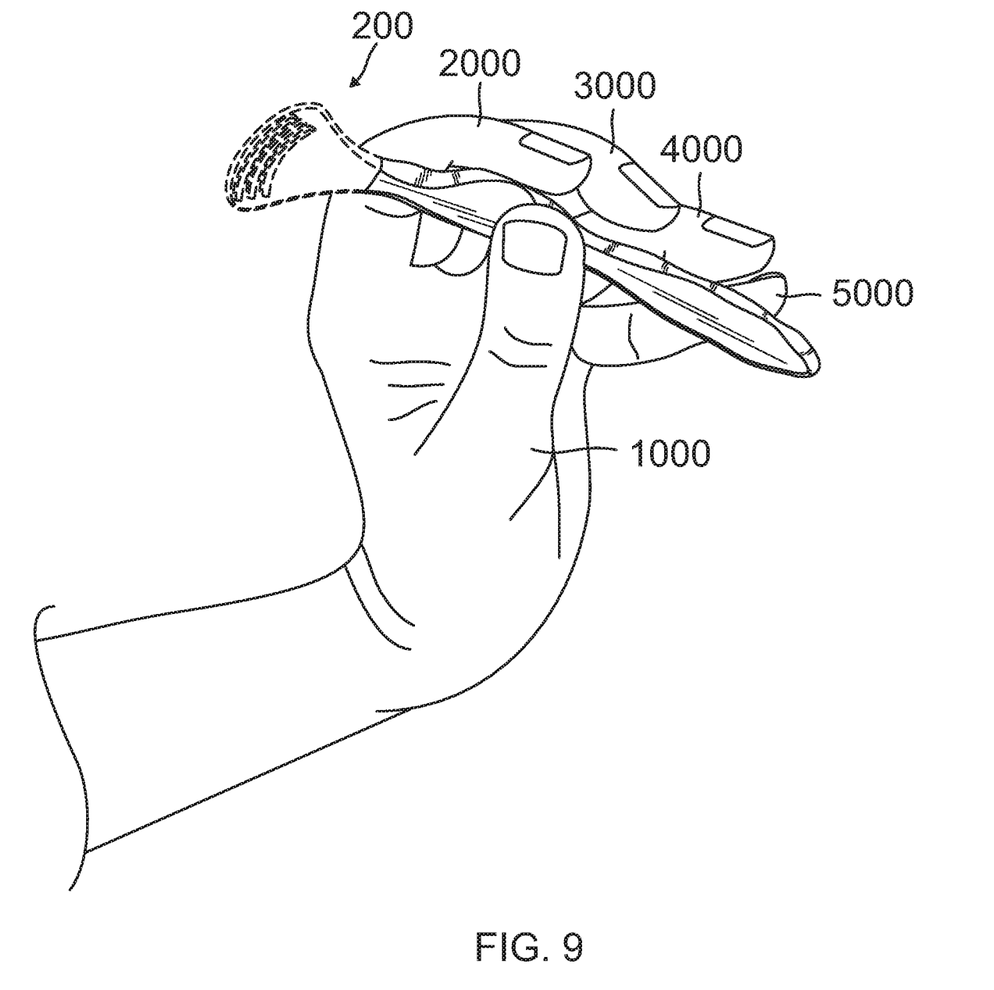
FIG. 9 is a bottom perspective view of one way to hold the ergonomic handle for a hand-operated personal use.

For the hand-operated personal use ergonomic tool 200, there are at least two ways in which the ergonomic tool 200 is held by the fingers of one hand, either left hand or right hand. Referring to FIG. 9, a right-handed person or left-handed person will place a forefinger 2000 in the first top cavity, a third or middle finger 3000 in the second top cavity, a fourth or ring finger 4000 in the third top third cavity, and the fifth or pinky finger 5000 in either the fourth top cavity 70C or in the fifth top cavity number 80C. The thumb 1000 is placed one the first bottom cavity 150C. Alternatively, a right-handed person or left-handed person will place a forefinger 2000 in the second top 50C, a third or middle finger 3000 in the third top cavity, a fourth or ring finger 4000 in the fourth top cavity number 70C, and the fifth or pinky finger 5000 in the fifth top cavity 80C. The thumb 1000 is placed into the first bottom cavity 150C.

The handle therefore enables a person to grip a personal use device with the hand in a much more secure manner than prior art handles.

The hand-operated personal use ergonomic tool 200 is selected from the group consisting of tongue scrapers, tooth brushes, safety razors, dental picks which dispense water, dental air flossers etc. The specific hand-operated personal use ergonomic tool 200 is illustrated in dashed lines and therefore specifically form no portion of the invention as it is the handle 10 that is being claimed as the innovative feature of the present invention.

Figure 5:
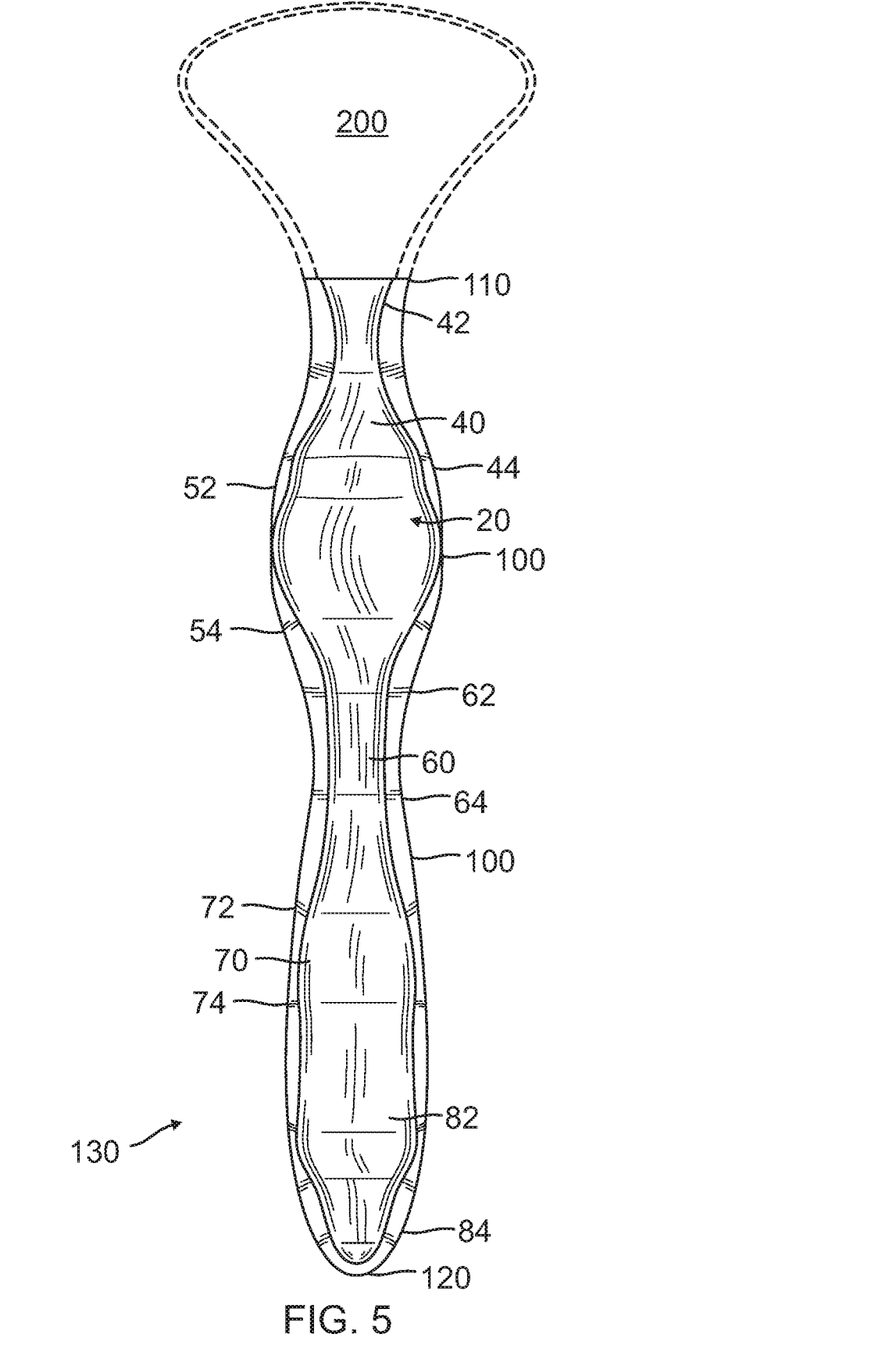
FIG. 5 is top plan view of the ergonomic handle for a hand-operated personal use tool.
Figure 6:
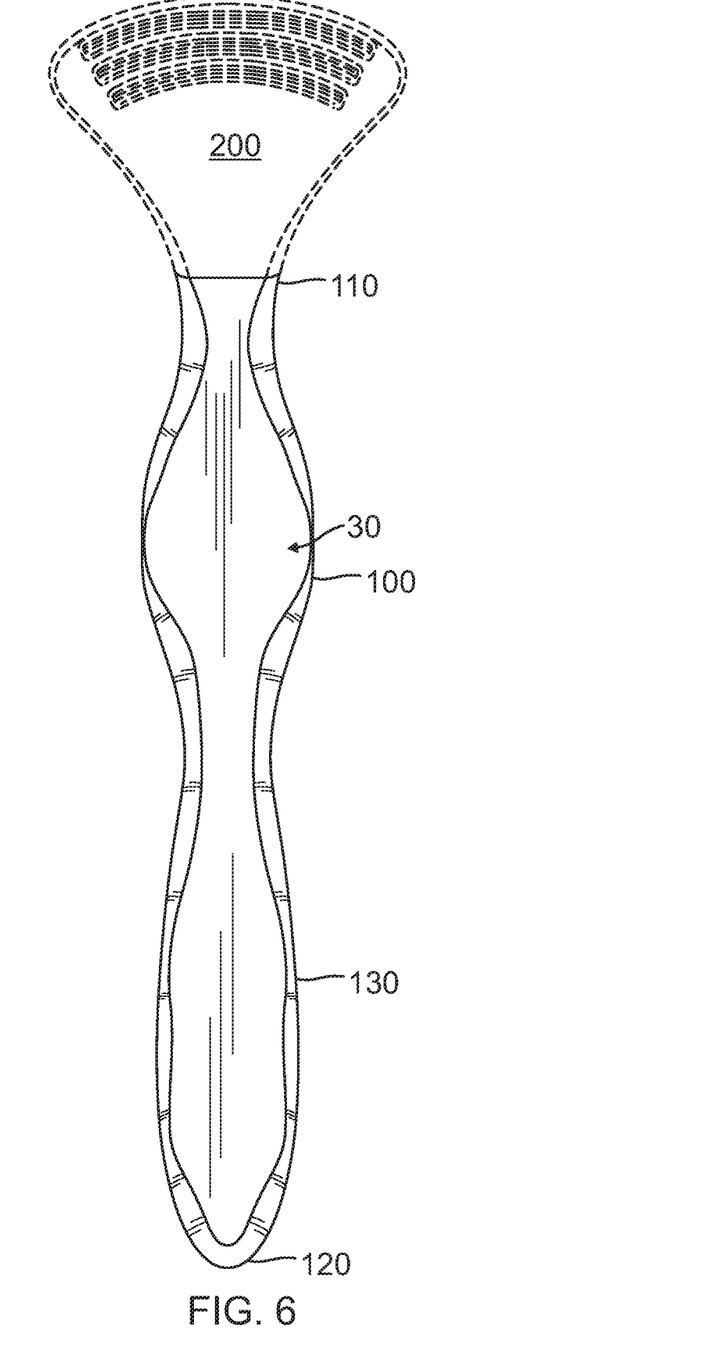
FIG. 6 is a bottom plan view of the ergonomic handle for a hand-operated personal use tool.

Viewed and described alternatively, for the upper surface 20, each of the cavities is bordered by its own separate transverse ridges forming the front and rear ridges to form the longitudinal sides of each respective cavity and separating each top cavity from an adjacent top protrusion. Referring to FIGS. 5 and 6, the first top cavity 40C is bounded by a first top cavity proximal transverse ridge 42 and first top cavity distal transverse ridge 44. The second top cavity 50C is bounded by a second top cavity proximal transverse ridge 52 and a second top cavity distal transverse ridge 54. The third to cavity 60C is bounded by a third top cavity proximal transverse ridge 62 and a third top cavity distal transverse ridge 64. The fourth top cavity 70C is bounded by a fourth top cavity proximal transverse ridge 72 and a fourth top cavity distal transverse ridge 74. The fifth top cavity 80C is bounded by a fifth top cavity proximal transverse ridge 82 and a fifth top cavity distal transverse ridge 84.

Referring to FIGS. 5 and 6, the entire ergonomic handle 10 is outlined with a smooth sidewall 100 extending along the entire circumference of the handle to facilitate the person placing the palm of their hand around the sidewall and having the thumb adjacent to or on the lower surface 30 when grasping the ergonomic handle 10 for a hand-operated personal use ergonomic tool 200. The ergonomic handle 10 has a first end 110 and a second end 120 with a body 130 in between said first end 110 and said second end 120. The first end 110 is affixed to said hand-operated personal use ergonomic tool 200. It is also within the spirit and scope of this invention for the hand operated personal use ergonomic tool 200 to be removably affixed to ergonomic handle 10.

Figure 7:
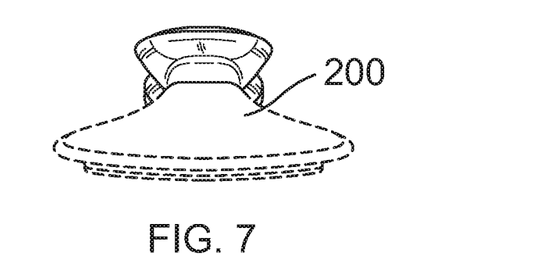
FIG. 7 is a front view of the ergonomic handle for a hand-operated personal use tool.
Figure 8:
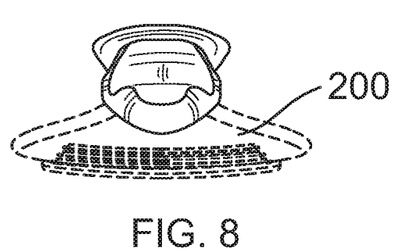
FIG. 8 is a rear view of the ergonomic handle for a hand-operated personal use tool.

Referring to FIGS. 7 and 8, there is illustrated a front view and a rear view respectively, of the present invention ergonomic handle 10. From these views the hand operated personal use ergonomic tool 200 is shown attached to the present invention ergonomic handle 10. The ergonomic handle 10 is made out of material selected from the group consisting of plastic and metal.

It is also within the spirit and scope of this invention to have a users's fingers be placed in any of the indentations that are most comfortable to the specific user. For example a larger handed person might find it more comfortable to place his or her pinky finger 5000 into the fifth top cavity 80C as opposed to the fourth top cavity 70C. Similarly, the indentations may be used to accept a user's fingers while wrapping around ergonomic handle 10 or simply placing one or more fingers over the top of the ergonomic handle 10.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An ergonomic handle adapted for use with a hand-operated personal use tool comprising:
   a. a top surface and a bottom surface having a generally arcuate shape;
   b. said ergonomic handle having a first end and a second end with a body in between said first end and said second end;
   c. said first end affixed to said hand-operated personal use tool;
   d. between the first end and the second end, the top surface of the ergonomic handle includes five spaced apart cavities and six spaced apart protrusions, which sequentially are a first top protrusion beginning at said front end, a first top cavity, a second top protrusion, a second top cavity, a third top protrusion, a third top cavity, a fourth top protrusion, a fourth top cavity, a fifth top protrusion, a fifth top cavity and a sixth top protrusion terminating in said rear end;
   e. the bottom surface is generally arcuate, the first top protrusion is enveloped on and within the body of the ergonomic handle and does not extend to the bottom surface, the first top cavity extends through the body of the ergonomic handle to the bottom surface to form a first bottom protrusion, the second top protrusion beginning at the bottom of the first cavity is aligned with the second top cavity and extends to the second bottom protrusion, a third top protrusion is aligned with the second bottom protrusion, a remainder of the bottom surface is flat and extends the second end which on the upper surface ends in the sixth top protrusion; and
   f. said ergonomic handle is outlined with a smooth sidewall extending along an entire circumference of the ergonomic handle.

2. The ergonomic handle in accordance with claim 1, further comprising: each respective upper cavity is bordered by its own separate transverse ridge forming a front and a rear ridge to form the longitudinal sides of each respective cavity and separating each top cavity from an adjacent top protrusion.

3. The ergonomic handle in accordance with claim 2, further comprising:
   a. the first top cavity is bounded by a first top cavity proximal transverse ridge and a first top cavity distal transverse ridge;

b. the second top cavity is bounded by a second top cavity proximal transverse ridge and a second top cavity distal transverse ridge;
c. the third top cavity is bounded by a third top cavity proximal transverse ridge and a third top cavity distal transverse ridge;
d. the fourth top cavity is bounded by a fourth top cavity proximal transverse ridge and a fourth top cavity distal transverse ridge; and
e. the fifth top cavity is bounded by a fifth top cavity proximal transverse ridge and a fifth top cavity distal transverse ridge.

4. The ergonomic handle in accordance with claim 1, further comprising: said first top cavity has a length between 0.3 inches and 1.5 inches, said second top cavity has a length between 0.3 inches and 1.5 inches, said third top cavity has a length between 0.3 inches and 1.5 inches, said fourth top cavity has a length between 0.3 inches and 1.5 inches, said fifth top cavity has a length between 0.3 inches and 1.5 inches.

5. The ergonomic handle in accordance with claim 4, further comprising: said bottom cavity has a length between 0.8 inches and 1.5 inches and a depth between 0.1 inch and 0.2 inch.

6. The ergonomic handle in accordance in claim 1, further comprising:
a. said first top cavity has an approximate length of 0.5 inches and an approximate depth of 0.1 inches;
b. said second top cavity has an approximate length of 0.65 inches and an approximate depth of 0.15 inches;
c. said third top cavity has an approximate length of 0.65 inches and an approximate depth of 0.15 inches;
d. said fourth top cavity has an approximate length of 0.55 inches and an approximate depth of 0.12 inches; and
e. said fifth top cavity has an approximate length of 0.4 inches and an approximate depth of 0.1 inches.

7. The ergonomic handle in accordance with claim 6, further comprising: said bottom cavity has a length of approximately 0.9 inches and a depth of approximately 0.15 inches.

8. The ergonomic handle in accordance with claim 1, further comprising; the ergonomic handle is made of material selected from the group consisting of: metal and plastic.

9. An ergonomic handle comprising:
a. an upper surface and a lower surface;
b. said ergonomic handle having a first end and a second end with a body in between said first end and said second end;
c. said first end affixed to an object;
d. said upper surface of said ergonomic handle including five spaced apart cavities formed into the upper surface of said body and aligned along said upper surface; and
e. said upper surface of said ergonomic handle including six spaced apart protrusions with a first protrusion adjacent said front end, a sixth protrusion adjacent said rear end, and a second through fourth protrusion respective spaced between a second and third cavity, a third and fourth cavity, and a fourth and fifth cavity.

10. The ergonomic handle in accordance with claim 9, further comprising: said lower surface contains a bottom cavity bounded by a first bottom protrusion and a second bottom protrusion.

11. The ergonomic handle in accordance with claim 9, further comprising: said lower surface is arcuate in shape.

12. The ergonomic handle in accordance with claim 9, further comprising: said ergonomic handle is outlined with a smooth sidewall extending along an entire circumference of the ergonomic handle.

13. The ergonomic handle in accordance with claim 9, further comprising: each respective upper cavity is bordered by its own separate transverse ridge forming a front and a rear ridge to form the longitudinal sides of each respective cavity and separating each top cavity from an adjacent top protrusion.

14. The ergonomic handle in accordance with claim 13, further comprising:
a. a first top cavity is bounded by a first top cavity proximal transverse ridge and a first top cavity distal transverse ridge;
b. a second top cavity is bounded by a second top cavity proximal transverse ridge and a second top cavity distal transverse ridge;
c. a third top cavity is bounded by a third top cavity proximal transverse ridge and a third top cavity distal transverse ridge;
d. a fourth top cavity is bounded by a fourth top cavity proximal transverse ridge and a fourth top cavity distal transverse ridge; and
e. a fifth top cavity is bounded by a fifth top cavity proximal transverse ridge and a fifth top cavity distal transverse ridge.

15. The ergonomic handle in accordance with claim 14, further comprising: said first top cavity has a length between 0.3 inches and 1.5 inches, said second top cavity has a length between 0.3 inches and 1.5 inches, said third top cavity has a length between 0.3 inches and 1.5 inches, said fourth top cavity has a length between 0.3 inches and 1.5 inches, said fifth top cavity has a length between 0.3 inches and 1.5 inches.

16. The ergonomic handle in accordance with claim 15, further comprising: said bottom cavity has a length between 0.8 inches and 1.5 inches and a depth between 0.1 inch and 0.2 inch.

17. The ergonomic handle in accordance in claim 14, further comprising:
a. said first top cavity has an approximate length of 0.5 inches and an approximate depth of 0.1 inches;
b. said second top cavity has an approximate length of 0.65 inches and an approximate depth of 0.15 inches;
c. said third top cavity has an approximate length of 0.65 inches and an approximate depth of 0.15 inches;
d. said fourth top cavity has an approximate length of 0.55 inches and an approximate depth of 0.12 inches; and
e. said fifth top cavity has an approximate length of 0.4 inches and an approximate depth of 0.1 inches.

18. The ergonomic handle in accordance with claim 17, further comprising: said bottom cavity has a length of approximately 0.9 inches and a depth of approximately 0.15 inches.

19. The ergonomic handle in accordance with claim 9, further comprising; the ergonomic handle is made of material selected from the group consisting of: metal and plastic.

* * * * *